United States Patent
Takahashi et al.

(10) Patent No.: US 10,974,224 B2
(45) Date of Patent: Apr. 13, 2021

(54) ACTIVATED CARBON, METAL-CARRYING ACTIVATED CARBON USING SAME AND HYDROGENATION REACTION CATALYST

(71) Applicant: KURARAY CO., LTD., Kurashiki (JP)

(72) Inventors: Keita Takahashi, Okayama (JP); Takayuki Yoshikawa, Okayama (JP); Takayuki Yamada, Okayama (JP)

(73) Assignee: KURARAY CO., LTD, Kurashiki (JP)

( * ) Notice: Subject to any disclaimer, the term of this patent is extended or adjusted under 35 U.S.C. 154(b) by 0 days.

(21) Appl. No.: 15/733,219

(22) PCT Filed: Dec. 17, 2018

(86) PCT No.: PCT/JP2018/046301
§ 371 (c)(1),
(2) Date: Jun. 11, 2020

(87) PCT Pub. No.: WO2019/131270
PCT Pub. Date: Jul. 4, 2019

(65) Prior Publication Data
US 2020/0384444 A1    Dec. 10, 2020

(30) Foreign Application Priority Data

Dec. 25, 2017 (JP) .............................. JP2017-247439

(51) Int. Cl.
| | | |
|---|---|---|
| *C01B 31/08* | (2006.01) | |
| *B01J 21/18* | (2006.01) | |
| *C01B 32/318* | (2017.01) | |
| *B01J 23/44* | (2006.01) | |
| *B01J 35/00* | (2006.01) | |
| *C01B 32/30* | (2017.01) | |

(52) U.S. Cl.
CPC .............. *B01J 21/18* (2013.01); *B01J 23/44* (2013.01); *B01J 35/0033* (2013.01); *C01B 32/30* (2017.08); *C01B 32/318* (2017.08); *C01P 2006/40* (2013.01); *C01P 2006/90* (2013.01)

(58) Field of Classification Search
CPC .............................. C01B 32/30; C01B 32/318
See application file for complete search history.

(56) References Cited

U.S. PATENT DOCUMENTS

| | | | |
|---|---|---|---|
| 6,475,461 B1 * | 11/2002 | Ohsaki ................... | H01G 11/34 423/445 R |
| 2013/0023405 A1 | 1/2013 | Hitomi et al. | |
| 2019/0329235 A1 | 10/2019 | Takahashi et al. | |

FOREIGN PATENT DOCUMENTS

| | | |
|---|---|---|
| JP | H06-269667 | 9/1994 |
| JP | 2001-035522 | 2/2001 |
| JP | 2011-136937 | 7/2011 |
| JP | 2013-163629 | 8/2013 |
| JP | 2016-159256 | 9/2016 |
| WO | 2008/053919 | 5/2008 |
| WO | 2011/125504 | 10/2011 |
| WO | 2018/116842 | 6/2018 |

OTHER PUBLICATIONS

International Search Report dated Feb. 5, 2019 in PCT/JP2018/046301 with English translation, 5 pages.
Written Opinion dated Feb. 5, 2019 in PCT/JP2018/046301.

* cited by examiner

*Primary Examiner* — Stuart L Hendrickson
(74) *Attorney, Agent, or Firm* — Grüneberg and Myers, PLLC

(57) ABSTRACT

The present invention relates to an activated carbon having an electric conductivity of 3.5 S/cm or more obtained by powder resistance measurement under a load of 12 kN and an oxygen content of 3.0% by mass or more, and a metal-carrying activated carbon using the same, and the like.

20 Claims, No Drawings

ACTIVATED CARBON, METAL-CARRYING ACTIVATED CARBON USING SAME AND HYDROGENATION REACTION CATALYST

TECHNICAL FIELD

The present invention relates to an activated carbon for carrying a catalyst, and a metal-carrying activated carbon using the same.

BACKGROUND ART

A catalytic hydrogenation reaction using a heterogeneous catalyst is one of important processes in the chemical industry, and is widely used industrially. A catalyst in which a metal catalyst such as a noble metal is carried on a carbon material such as an activated carbon is widely used in industrial processes such as a hydrogenation reaction and a dehydrogenation reaction.

A carbon material used for a catalyst carrier is often subjected to an oxidation treatment in order to improve the reaction efficiency of a hydrogenation reaction or the like due to the microparticulation of a metal catalyst to be carried. For example, Patent Literature 1 discloses that an activated carbon is previously heat-treated (oxidized) at 300 to 500° C. in air, and then subjected to an ion exchange method to form a surface functional group, and a carried catalyst (metal) is subjected to microparticulation to improve a catalytic reaction efficiency.

However, the microparticulation of the metal catalyst by the oxidation treatment as described in Patent Literature 1 has been limited, and the performance of the obtained catalyst has never been satisfactory. It is also important to increase the specific surface area of the carbon material for improving the catalytic performance, but the increase in the specific surface area is limited. The cost is also increased by further increasing the specific surface area, so that the reaction efficiency is also desired to be improved by adjusting physical properties other than the specific surface area.

CITATION LIST

Patent Literature

Patent Literature 1: Japanese Unexamined Patent Publication No. H06-269667

SUMMARY OF INVENTION

An activated carbon according to one aspect of the present invention has an electric conductivity of 3.5 S/cm or more obtained by powder resistance measurement under a load of 12 kN and an oxygen content of 3.0% by mass or more.

DESCRIPTION OF EMBODIMENTS

The present invention has been made in view of the above-described problems, and it is an object of the present invention to provide a catalyst-carrying activated carbon which can improve catalytic performance without increasing a specific surface area while the micronization of a metal is almost the same as that of the conventional technique, and a metal-carrying activated carbon using the same.

The present inventors have conducted detailed studies in order to solve the above-described problems. As a result, the present inventors have found that the problems can be solved by the following configuration, and have completed the present invention by further studying based on this finding.

Hereinafter, embodiments of the present invention will be described in detail. The scope of the present invention is not limited to the embodiments described here, and various changes will be possible without departing from the spirit of the invention.

[Activated Carbon]

An activated carbon of the present embodiment has an electric conductivity of 3.5 S/cm or more obtained by powder resistance measurement under a load of 12 kN and an oxygen content of 3.0% by mass or more.

The activated carbon of the present embodiment has the above configuration, which can exhibit extremely excellent catalytic performance. By using the activated carbon of the present invention as a carrier for a metal catalyst, the catalytic performance can be improved without increasing the specific surface area while the microparticulation of the metal is at the same level as that of the conventional technique. That is, the present invention can provide a catalyst-carrying activated carbon having suppressed cost and excellent catalytic performance.

The electric conductivity of the activated carbon of the present embodiment is 3.5 S/cm or more as described above. By setting the electric conductivity within the above range, the interaction between the metal catalyst to be described later and the activated carbon is presumed to be changed, to improve the catalytic performance. The electric conductivity is more preferably 5.0 S/cm or more, and still more preferably 6.0 S/cm or more.

Meanwhile, in the activated carbon of the present embodiment, the upper limit of the electric conductivity is not particularly limited. However, if the electric conductivity is too large, the excessive development of a carbon structure causes an activation treatment to require time, which is not economically preferable. If the electric conductivity is too high, an oxidation treatment may be difficult. In such a case, the degree of dispersion of the metal catalyst becomes low, which is not preferable. Therefore, the electric conductivity of the activated carbon of the present embodiment is preferably 15 S/cm or less, more preferably 13 S/cm or less, and still more preferably 10 S/cm or less.

In the present embodiment, "electric conductivity" means the electric conductivity of an activated carbon obtained by powder resistance measurement under a load of 12 kN. The activated carbon is pulverized to have a predetermined particle size (particle size distribution). The measurement of the electric conductivity is largely influenced by the particle size of a measurement sample, whereby the electric conductivity can be specifically measured by a measurement method described in Examples to be described later.

The oxygen content of the activated carbon of the present embodiment is 3.0% by mass or more. If the oxygen content is 3.0% by mass or more, the degree of dispersion of the metal catalyst is sufficiently obtained (the microparticulation of the metal catalyst becomes sufficient), whereby the reaction efficiency of a hydrogenation reaction is improved. The oxygen content is more preferably 4.0% by mass or more, and still more preferably 5.0% by mass or more.

Meanwhile, the upper limit of the oxygen content in the activated carbon of the present embodiment is not particularly limited. However, if the oxygen content is too large, carbon consumption increases, so that the yield of the activated carbon decreases, which is not preferable from the economic viewpoint. If the oxygen content is too high, the hardness of the activated carbon decreases, so that the carried metal falls off because of the pulverization, which is not preferable also from the point. Therefore, the oxygen content of the activated carbon of the present invention is preferably 20.0% by mass or less, more preferably 15.0% by mass or less, and still more preferably 10.0% by mass or less.

In the present embodiment, the "oxygen content" means the amount of oxygen in the pulverized and dried activated carbon, and can be specifically measured by a measurement method described in Examples to be described later.

The BET specific surface area of the activated carbon of the present embodiment is not particularly limited. However, it is preferably 1000 $m^2/g$ or more, more preferably 1300 $m^2/g$ or more, and still more preferably 1600 $m^2/g$ or more. It is considered that, if the BET specific surface area is 1000 $m^2/g$ or more, the adsorption of a reaction compound is sufficiently obtained to improve the reaction efficiency of the hydrogenation reaction. Meanwhile, in the activated carbon of the present embodiment, the upper limit of the BET specific surface area is not particularly limited. However, if the BET specific surface area is too large, the yield of the obtained activated carbon decreases, which is not preferable from the economic viewpoint. Therefore, the BET specific surface area of the activated carbon of the present invention is preferably 2200 $m^2/g$ or less, more preferably 2100 $m^2/g$ or less, and still more preferably 2000 $m^2/g$ or less.

In the present embodiment, the specific surface area refers to a BET specific surface area calculated by a nitrogen adsorption method. The method for measuring the specific surface area can include a known method, and examples thereof include a method in which nitrogen adsorption isotherm measurement is performed and the specific surface area is calculated from the obtained adsorption isotherm. More specifically, the specific surface area can be measured by a method described in Examples.

The average pore size of micropores of the activated carbon of the present embodiment is not particularly limited. However, it is preferably 1.55 nm or more, more preferably 1.60 nm or more, and still more preferably 1.65 nm or more. It is considered that, if the average pore size of micropores is 1.55 nm or more, the diffusion of the reaction compound in catalyst particles is improved to improve the hydrogenation reaction efficiency. Meanwhile, in the activated carbon of the present embodiment, the upper limit of the average pore size of micropores is not particularly limited. However, if the average pore size of micropores is too large, the yield of the obtained activated carbon decreases, which is not preferable from the economic viewpoint. Therefore, the average pore size of micropores of the activated carbon of the present invention is preferably 1.90 nm or less, more preferably 1.85 nm or less, and still more preferably 1.80 nm or less.

In the present embodiment, the average pore size of micropores is calculated by a nitrogen adsorption method, and can be measured by a known method. Specific examples of the measurement method include a method in which nitrogen adsorption isotherm measurement is performed and the average pore size of micropores is calculated from the obtained adsorption isotherm. More specifically, the average pore size of micropores can be measured by a method described in Examples.

In the present embodiment, the shape of the activated carbon is not particularly limited. However, it is preferably any of granular, powdery, fibrous, pellet, and spherical shapes. The shape of the activated carbon can be appropriately selected depending on the application, but it is typically a granular or powdery shape. In particular, the activated carbon preferably has a powder shape having high carrying performance per volume.

For the pulverization, for example, a jaw crusher, a hammer mill, a pin mill, a roller mill, a rod mill, a ball mill, a jet mill, and the like may be used.

In the present embodiment, the size of the activated carbon is preferably set such that the average particle size (D50) of the activated carbon is about 150 µm to 5 mm in the case of the granular shape or the like, and the average particle size (D50) of the activated carbon is about 1 to 100 µm in the case of the powdery shape or the like.

In the present embodiment, the numerical value of the above D50 is a value measured by a laser diffraction measurement method in the same manner as in Examples to be described later, and the measurement is carried out, for example, with a wet particle size distribution measuring device (MICROTRAC MT3300EX II) manufactured by Nikkiso Co., Ltd., or the like.

[Method for Producing Activated Carbon]

The activated carbon of the present embodiment as described above can be obtained by carbonizing a carbonaceous material, heat-treating the obtained carbonized product at a temperature of 1100° C. or higher, then activating the heat-treated product in an atmosphere of a mixed gas containing water vapor, nitrogen, and carbon dioxide, and then oxidizing the activated product in an oxidizing atmosphere. That is, the present invention also includes a method for producing an activated carbon, which includes at least a step of heat-treating a carbonized product of a carbonaceous material at a temperature of 1100° C. or higher, an activation treatment step, and an oxidation treatment step.

(Carbonaceous Material)

The carbonaceous material can be selected from all known materials, and examples thereof include plants (coconut shell, chaff, coffee grounds, wood, and the like), natural polymers (starch, cellulose, lignins, and the like), semisynthetic polymers (cellulose esters, cellulose ethers, lignin resins, and the like), synthetic polymers (phenolic resins, furan-based resins, epoxy resins, and the like), and natural minerals. These raw materials can be used alone or in combination of two or more. The preferable raw material is a plant raw material such as wood, and coconut shell having less impurities is more preferable.

The palm used as a raw material for the coconut shell is not particularly limited, and examples of the palm include oil palm, coconut palm, salak, and double coconut palm. Coconut shells obtained from these palms may be used alone or in combination of two or more. Among these coconut shells, coconut shell derived from coconut palm or oil palm which is a biomass waste produced in a large quantity, and is utilized as a food, a detergent raw material, a biodiesel oil raw material, and the like is particularly preferable, because the coconut shell is readily available and is inexpensive.

Each of these coconut shells is available in the form of a char (coconut shell char) which is produced by temporarily calcining each of the coconut shells, and it is preferable to use the char as a crude raw material. The term "char" generally refers to a powdery solid which is produced in a non-molten and unsoftened form by heating a coal and is rich in a carbon content. In the present invention, the term "char" also refers to a powdery solid which is produced in a non-molted and unsoftened form by heating an organic material and is rich in a carbon content. The method for producing the char from the coconut shell is not particularly limited, and the char can be produced by any method known in the prior art. For example, by firing (carbonizing) the coconut shell as a raw material at a temperature of about 400 to 800° C. under an atmosphere of an inert gas, such as nitrogen, carbon dioxide, helium, argon, carbon monoxide, or a fuel combustion gas, a mixed gas of these inert gases, or a mixed gas of any of the inert gases as a main component and other gas, a carbonized product of a carbonaceous material can be produced.

(Heat Treatment Step)

The heat treatment of the carbonized product can be carried out by heating the carbonized material at a temperature of 1100° C. or higher, and preferably 1200° C. or higher in the absence of oxygen or air. If the heat treatment temperature is too low, the electric conductivity of the activated carbon is low, so that the interaction between the metal catalyst and the activated carbon is insufficient, which causes deteriorated catalytic performance. As the heat treatment temperature is higher, the electric conductivity of the activated carbon is higher, but an activation time for obtaining a sufficient specific surface area is longer. This causes increased production cost, which is not preferable. Therefore, the upper limit of the heat treatment temperature is preferably 1500° C. or lower.

Heating means is not particularly limited. However, for example, the heating can be performed using an electric furnace or the like.

(Activating Step)

The activation treatment can be carried out by a method common in the art to which the present invention belongs, and main examples thereof include two types of treatment methods, i.e., a gas activation treatment and a chemical activation treatment.

As the gas activation treatment, a method is known, in which an activated carbon precursor is heated in the presence of, for example, water vapor, carbon dioxide, air, oxygen, a combustion gas, or a mixed gas thereof. As the chemical activation treatment, a method is known, in which an activator such as zinc chloride, calcium chloride, phosphoric acid, sulfuric acid, sodium hydroxide, potassium hydroxide, magnesium hydroxide, or calcium hydroxide, is mixed with an activated carbon precursor and the resultant mixture is then heated under an inert gas atmosphere. In the present embodiment, it is preferable to use the gas activation treatment, because any step of removing a remaining chemical substance is needed in the chemical activation treatment and therefore the production method is complicated.

The gas activation treatment can be performed by using a fluidized bed, a multistage furnace, a rotary furnace, or the like at a temperature of 850° C. or higher, preferably 850 to 1000° C. (for example, 850 to 950° C.) in an atmosphere of a mixture of water vapor, nitrogen, and carbon dioxide. By activating in the atmosphere of the mixture, the carbonized product is partially gasified, to obtain an activated carbon. The gas (mixed gas composed of water vapor, nitrogen, and carbon dioxide) for gasifying a part of the carbonized product of the carbonaceous material can be also obtained by burning other combustible materials including natural gas, petroleum, or hydrocarbon. The activation temperature is typically varied in the range of about 25° C. in many cases.

The activation time is not particularly limited. However, it may be about 0.5 to 48 hours, preferably about 1 to 24 hours, and more preferably about 2 to 20 hours (for example, 6 to 12 hours). If the activation time is too short, a sufficient specific surface area cannot be obtained, which causes deteriorated catalytic performance after a metal is carried. If the activation time is too long, the productivity may be deteriorated.

The gas partial pressure is not particularly limited. However, the water vapor partial pressure is 7.5 to 40%, and preferably 10 to 30% (for example, 10 to 20%); the carbon dioxide partial pressure is 10 to 50%, and preferably 15 to 45% (for example, 20 to 40%); and the nitrogen partial pressure is about 30 to 80%, and preferably about 40 to 70% (for example, 45 to 65%). The gas partial pressure may be set such that the water vapor partial pressure is about 10 to 40%; the carbon dioxide partial pressure is about 10 to 40%; and the nitrogen partial pressure is about 40 to 80%. The gas total pressure is generally 1 atm (about 0.1 MPa).

The total gas supply amount (flow rate) is not particularly limited. However, it is about 1 to 50 L/min, and preferably about 1 to 25 L/min, with respect to 100 g of the carbonized product raw material.

(Acid-Washing Step)

The step of producing the activated carbon of the present embodiment may include an acid-washing step. The acid-washing step is a step of removing impurities such as metal components contained in the activated carbon by washing the activated carbon after the activation treatment with a washing solution containing an acid. The acid-washing can be performed, for example, by immersing a raw material activated carbon in a washing solution containing an acid. In the acid-washing step, the raw material activated carbon may be washed with hydrochloric acid, and then washed with water, or appropriate combination of water-washing and acid-washing such as repetition of acid-washing and water-washing may be used.

As the acid-washing solution, inorganic acids such as hydrochloric acid, sulfuric acid, and nitric acid, and organic acids such as saturated carboxylic acids (such as formic acid, acetic acid, propionic acid, oxalic acid, tartaric acid, and citric acid), and aromatic carboxylic acids (such as benzoic acid and terephthalic acid) are preferably used. Among these, hydrochloric acid is more preferably used for washing. When the hydrochloric acid is used as the acid-washing solution, the concentration of the hydrochloric acid is preferably 0.1 to 3.0% by mass, and more preferably 0.3 to 1.0% by mass. If the concentration of the hydrochloric acid is too low, it is necessary to increase the number of acid-washings in order to remove impurities. Conversely, if the concentration of the hydrochloric acid is too high, the remaining hydrochloric acid increases. Therefore, the concentration of the range allows an efficient acid-washing step, which is preferable in terms of the productivity.

The temperature of the solution during acid-washing or water-washing is not particularly limited. However, it is preferably 0 to 98° C., more preferably 10 to 95° C., and still more preferably 15 to 90° C. The temperature of the washing solution into which the raw material activated carbon is immersed is desirably in the range since this allows the washing to be performed with a practical time and a load on equipment being reduced.

(Oxidation Treatment Step)

A method for producing an activated carbon of the present embodiment includes an oxidation treatment step. The oxidation treatment step is a step of increasing the oxygen content of the activated carbon by subjecting the activated carbon to an oxidation treatment in an oxidizing atmosphere. Specific examples thereof include a method in which a heat treatment is performed in a mixed gas atmosphere containing oxygen, and a method in which a treatment is performed with an oxidizing agent such as hydrogen peroxide water, nitric acid, or potassium permanganate.

The oxidation treatment using oxygen can be performed using a fluidized bed, a multistage furnace, or a rotary furnace or the like similar to that in the activation treatment, and can be performed at a temperature of 400° C. or higher, and preferably 400 to 600° C. If the oxidation treatment temperature is lower than 400° C., the oxidation of the activated carbon does not sufficiently proceed. If the oxidation treatment temperature is 600° C. or higher, the oxidation of the activated carbon rapidly proceeds. This causes intense carbon consumption, so that the yield decreases, which is not preferable.

An oxidation treatment time is not particularly limited. However, it may be about 0.1 to 3 hours, preferably about 0.2 to 2 hours, and more preferably about 0.3 to 1 hour. If the oxidation treatment time is too short, the oxidation of the activated carbon does not sufficiently proceed. If the oxidation treatment time is too long, the productivity decreases.

The gas partial pressure is not particularly limited. However, the gas partial pressure may be set such that the oxygen partial pressure is about 1 to 15%; the water vapor partial pressure is about 5 to 15%; the carbon dioxide partial pressure is about 5 to 15%; and the nitrogen partial pressure is about 50 to 80%. The gas total pressure is typically 1 atm (about 0.1 MPa).

The total gas supply amount (flow rate) is not particularly limited. However, it is 1 to 100 L/min, and preferably about 1 to 50 L/min with respect to 50 g of an activated product raw material.

[Metal-Carrying Activated Carbon]

A metal-carrying activated carbon of the present embodiment is characterized in that a metal serving as a catalyst is carried on the above-described activated carbon.

The metal to be carried is not particularly limited. However, examples thereof include a metal used as a catalyst for a hydrogenation reaction or a dehydrogenation reaction. Specific examples thereof include palladium, platinum, ruthenium, rhodium, osmium, iridium, nickel, cobalt, rhenium, vanadium, tungsten, molybdenum, iron, and titanium. Platinum group elements (palladium, platinum, ruthenium, rhodium, osmium, and iridium), nickel, and iron are more preferable. Among these, palladium or platinum is suitable. These can be used alone or in combination of two or more.

The amount of the metal carried on the metal-carrying activated carbon of the present embodiment is not particularly limited. However, it is preferably 0.1 to 50% by mass, and particularly preferably 0.5 to 10% by mass.

The metal-carrying activated carbon of the present embodiment can be prepared by a known method. For example, the metal-carrying activated carbon can be produced by a method in which a precursor for a metal serving as a catalyst is adsorbed on an activated carbon as described above, and then subjected to a reduction treatment.

Examples of the precursor for the metal (metal component) which can be used for the metal-carrying activated carbon of the present embodiment include a metal chloride, a bromide, a fluoride, a hydroxide, a nitrate, an acetate, a carbonate, a sulfate, and an ammonium salt. These can be used alone or at an optional ratio in combination of two or more. Examples of a precursor for a palladium catalyst include palladium chloride, palladium nitrate, and palladium acetate.

Examples of the method in which the metal precursor is adsorbed on the activated carbon include (i) an impregnation method in which an activated carbon is suspended in a precursor solution of a metal component, and a solvent is then distilled off from the resulting suspension, (ii) a precipitation method in which an activated carbon is suspended in the precursor solution, and the precursor solution is brought into contact with a precipitant to produce a precipitate such as a metal hydroxide on the surface of the activated carbon, (iii) an ion exchange method in which an acid point or base point of an activated carbon is subjected to ion exchange with a metal ion, (iv) a spray method in which the precursor solution is sprayed onto the activated carbon for impregnation under a reduced-pressure condition, and (v) an incipient wetness method in which an activated carbon is exhausted, and the precursor solution is then added little by little thereto so as to impregnate the same volume of the precursor solution as the pore volume of the activated carbon thereinto. Among these, from the viewpoints of dispersibility of the metal component and workability, the impregnation method, the precipitation method, and the ion exchange method are preferable, and the impregnation method and the precipitation method are more preferable. The order of adsorbing precursors of a plurality of metal components on an activated carbon is not particularly limited. The precursors of the metal components may be simultaneously adsorbed, or the precursors of the individual components may be separately adsorbed.

The precursor of the metal component is adsorbed on the activated carbon, and a reduction treatment is then performed, whereby a metal-carrying activated carbon can be obtained. The reduction treatment method is not limited to any of a liquid phase method and a gas phase method, but the liquid phase method is preferable. Examples of a reducing agent to be used include hydrogen, formaldehyde, methanol, sodium borohydride, and hydrazine. The solvent is preferably water, and other solvents miscible with water may be used in combination. A reduction temperature is preferably from room temperature to 100° C.

The metal-carrying activated carbon of the present embodiment can be suitably used for a hydrogenation reaction catalyst. A method in which the hydrogenation reaction is performed using the metal-carrying activated carbon of the present embodiment is not particularly limited, and a hydrogen source and a metal-carrying activated carbon may be brought into contact with an object (reaction substrate) to allow a hydrogenation reaction or a dehydrogenation reaction to be caused on the object.

Examples of the hydrogen source include reducing gases such as hydrogen; alcohols such as methanol, ethanol, and propanol; and hydrazines such as hydrazine, methylhydrazine, allylhydrazine, and phenylhydrazine, and derivatives and salts thereof. Among these hydrogen sources, hydrogen is preferably used.

The amount of the hydrogen source to be used is preferably 10 to 2000 mol per 1 mol of the object (reaction substrate).

The amount of the metal-carrying activated carbon of the present embodiment used in the hydrogenation reaction is preferably set, for example, such that the amount of the carried metal is 0.0001 to 1 mol per 1 mol of the object (reaction substrate).

The metal-carrying activated carbon of the present embodiment is extremely useful as a catalyst for the hydrogenation reaction, whereby the metal-carrying activated carbon exhibits excellent effects in various industrial processes.

As described above, the present specification discloses techniques of various aspects, among which main techniques are summarized below.

That is, an activated carbon according to one aspect of the present invention has an electric conductivity of 3.5 S/cm or more obtained by powder resistance measurement under a load of 12 kN and an oxygen content of 3.0%/a by mass or more.

Such a configuration makes it possible to provide an activated carbon having extremely excellent catalytic performance.

It is preferable that the activated carbon is derived from coconut shell. Thereby, it is considered that the above effect can be more reliably obtained.

Furthermore, in the metal-carrying activated carbon according to another aspect of the present invention, a metal is carried on the activated carbon described above. Such a configuration makes it possible to provide a metal-carrying activated carbon having extremely excellent catalytic performance.

In the metal-carrying activated carbon, the metal is preferably palladium. Thereby, it is considered that the above effect can be more reliably obtained.

It is considered that the metal-carrying activated carbon is more effective when it is used in a hydrogenation reaction catalyst.

EXAMPLES

Hereinafter, the present invention will be described in more detail based on Examples, but the following Examples do not limit the present invention at all.

First, a method for evaluating the characteristics of each activated carbon will be described.

[Measurement of Electric Conductivity of Activated Carbon]

An electric conductivity of an activated carbon was measured using a powder resistance measuring unit "MCP-PD51" manufactured by Mitsubishi Chemical Analytech Co., Ltd. Since the particle size of a measurement sample has a large influence on the measurement of electric conductivity, the sample is pulverized so that a 10% particle diameter (D10) of cumulative distribution on the volume basis of the activated carbon is about 1 to 3 µm, a 50% particle diameter (D50) of cumulative distribution on the volume basis is about 5 to 8 µm, and a 90% particle diameter (D90) of cumulative distribution on the volume basis is about 10 to 20 µm, and an electric conductivity of an activated carbon pellet when a load of 12 kN was then applied was measured. The particle size of the pulverized activated carbon was measured by a laser diffraction measurement method. That is, the activated carbon to be measured was placed in ion exchange water together with a surfactant, subjected to ultrasonic vibration to prepare a homogeneous dispersion, and the dispersion was measured using Microtrac MT 3300 EX-11 manufactured by MicrotracBEL Corp. "Polyoxyethylene (10) octylphenyl ether" manufactured by Wako Pure Chemical Industries, Ltd. was used as the surfactant. The analysis conditions are shown below.

(Analysis Conditions)
Number of measurements: 3 times
Measurement time: 30 seconds
Distribution representation: volume
Particle size division; standard
Calculation mode: MT 3000 II
Solvent name: WATER
Measurement upper limit: 2000 µm and measurement lower limit: 0.021 µm
Residual fraction ratio: 0.00
Passing fraction ratio: 0.00
Residual fraction ratio setting: invalid
Particle transmittance: absorption
Particle refractive index: N/A
Particle shape: N/A
Solvent refractive index: 1.333
DV value: 0.0100 to 0.0500
Transmittance (TR): 0.750 to 0.920

[Measurement of Oxygen Content of Activated Carbon]

The pulverized activated carbon was vacuum-dried at 120° C. for 2 hours, and the oxygen content of the activated carbon was then measured by Vario EL III manufactured by ELEMENTAR using benzoic acid as a reference material.

[Measurement of Specific Surface Area of Activated Carbon]

Using BELSORP-max manufactured by MicrotracBEL Corp., an activated carbon as a sample was heated under a nitrogen stream (nitrogen flow rate: 50 mL/min) at 300° C. for 3 hours, and the nitrogen adsorption-desorption isotherm of the activated carbon was then measured at 77 K. The obtained adsorption-desorption isotherm was analyzed by a multi-point BET method, and the specific surface area was calculated from a straight line in a region of relative pressure $P/P_0$=0.01 to 0.1 on the obtained curve.

[Measurement of Average Pore Size of Micropores of Activated Carbon]

The nitrogen adsorption-desorption isotherm obtained according to the method for measuring the specific surface area of the activated carbon was analyzed by the MP method, and the average pore size of micropores was calculated from the obtained pore volume of micropores and specific surface area of micropores according to the following equation.

$$D=4000\times V/S$$

(In the equation, D: average pore size of micropores (nm), V: pore volume of micropores (mL/g), S: specific surface area of micropores (m$^2$/g))

[Measurement of Benzene Adsorption Performance of Activated Carbon]

Benzene adsorption performance of an activated carbon after an activation treatment was measured in accordance with JIS K 1474 (1991) which was an activated carbon test method in Japanese Industrial Standards. At 25° C., air containing solvent vapor having a concentration of 1/10 of a solvent saturation concentration was caused to pass through a granular sample, and equilibrium adsorption performance was determined from the increase in the weight of the sample when the mass became constant.

Example 1

100 g of a coconut shell char was charged into a furnace, and heat-treated at 1300° C. while air was shut off. Thereafter, 80 g of the heat-treated product was charged into a fluidized furnace, and a mixed gas having a water vapor partial pressure of 15%, a carbon dioxide partial pressure of 11%, and a nitrogen partial pressure of 74% was supplied into the furnace at a total pressure of the gas of 1 atm and at a flow rate of 20 L/min. An activation time was adjusted under conditions of an activation temperature of 950° C. so that the benzene adsorption performance was 21.8%, to perform an activation treatment. Then, the activated product was washed with hydrochloric acid (concentration: 1 N, diluent: ion exchange water) at a temperature of 70° C. for 30 minutes and then thoroughly washed with ion exchange water for removal of residual acid, after which the resultant was dried to obtain an acid-washed activated carbon. Then, the acid-washed activated carbon was charged into a fluidized furnace having a furnace temperature set to 500° C., and a mixed gas having an oxygen partial pressure of 7%, a water vapor partial pressure of 11%, a carbon dioxide partial pressure of 8%, and a nitrogen partial pressure of 74% was supplied into the furnace at a total pressure of the gas of 1 atm and a flow rate of 30 L/min. While a heat treatment temperature was raised to 550° C., an oxidation treatment was performed until a yield was 90% to obtain an activated carbon. The specific surface area, electric conductivity, and oxygen content (O content) of the obtained activated carbon were as shown in Table 1.

Example 2

An activated carbon was produced in the same manner as in Example 1 except that an activation time was adjusted so that benzene adsorption performance after activation was 30.9%. The specific surface area, electric conductivity, and oxygen content of the obtained activated carbon were as shown in Table 1.

Example 3

An activated carbon was produced in the same manner as in Example 1 except that an activation time was adjusted so that benzene adsorption performance after activation was 45.0%. The specific surface area, electric conductivity, and oxygen content of the obtained activated carbon were as shown in Table 1.

Example 4

An activated carbon was produced in the same manner as in Example 1 except that an activation time was adjusted so that benzene adsorption performance after activation was 59.6%. The specific surface area, electric conductivity, and oxygen content of the obtained activated carbon were as shown in Table 1.

Example 5

An activated carbon was produced in the same manner as in Example 1 except that a heat treatment temperature of a coconut shell char was 1200° C. and an activation time was adjusted so that benzene adsorption performance after activation was 31.1%. The specific surface area, electric conductivity, and oxygen content of the obtained activated carbon were as shown in Table 1.

Example 6

An activated carbon was produced in the same manner as in Example 1 except that a heat treatment temperature of a coconut shell char was 1100° C. and an activation time was adjusted so that benzene adsorption performance after activation was 29.9%. The specific surface area, electric conductivity, and oxygen content of the obtained activated carbon were as shown in Table 1.

Example 7

An activated carbon was produced in the same manner as in Example 1 except that an activation time was adjusted so that benzene adsorption performance after activation was 30.9%, and an oxidation treatment was performed until a yield was 95.4%. The specific surface area, electric conductivity, and oxygen content of the obtained activated carbon were as shown in Table 1.

Comparative Example 1

An activated carbon was produced in the same manner as in Example 1 except that a coconut shell char was placed in a furnace without being subjected to a heat treatment, and an activation time was adjusted so that benzene adsorption performance after activation was 21.2%. The specific surface area, electric conductivity, and oxygen content of the obtained activated carbon were as shown in Table 1.

Comparative Example 2

An activated carbon was produced in the same manner as in Example 1 except that a coconut shell char was placed in a furnace without being subjected to a heat treatment, and an activation time was adjusted so that benzene adsorption performance after activation was 31.6%. The specific surface area, electric conductivity, and oxygen content of the obtained activated carbon were as shown in Table 1.

Comparative Example 3

An activated carbon was produced in the same manner as in Example 1 except that a coconut shell char was placed in a furnace without being subjected to a heat treatment, and an activation time was adjusted so that benzene adsorption performance after activation was 46.0%. The specific surface area, electric conductivity, and oxygen content of the obtained activated carbon were as shown in Table 1.

Comparative Example 4

An activated carbon was produced in the same manner as in Example 1 except that a coconut shell char was placed in a furnace without being subjected to a heat treatment, and an activation time was adjusted so that benzene adsorption performance after activation was 60.9%. The specific surface area, electric conductivity, and oxygen content of the obtained activated carbon were as shown in Table 1.

Comparative Example 5

An activated carbon was produced in the same manner as in Example 1 except that an activation time was adjusted so that benzene adsorption performance after activation was 31.0%, and an air oxidation treatment was not performed. The specific surface area, electric conductivity, and oxygen content of the obtained activated carbon were as shown in Table 1.

Table 1 summarizes the physical properties of the activated carbons obtained in Examples 1 to 7 and Comparative Examples 1 to 5.

TABLE 1

|  | Heat treatment | Specific surface area [m$^2$/g] | Electric conductivity [S/cm] | O content [mass %] | Average pore size of micropores [nm] |
|---|---|---|---|---|---|
| Example 1 | 1300° C. | 1092 | 12.87 | 5.44 | 1.57 |
| Example 2 | 1300° C. | 1381 | 8.59 | 7.11 | 1.68 |
| Example 3 | 1300° C. | 1625 | 5.08 | 7.14 | 1.81 |

TABLE 1-continued

|  | Heat treatment | Specific surface area [m²/g] | Electric conductivity [S/cm] | O content [mass %] | Average pore size of micropores [nm] |
|---|---|---|---|---|---|
| Example 4 | 1300° C. | 1901 | 4.53 | 7.16 | 1.87 |
| Example 5 | 1200° C. | 1377 | 6.97 | 8.80 | 1.65 |
| Example 6 | 1100° C. | 1351 | 6.12 | 8.28 | 1.59 |
| Example 7 | 1300° C. | 1256 | 12.69 | 4.36 | 1.60 |
| Comparative Example 1 | None | 1081 | 3.09 | 9.48 | 1.54 |
| Comparative Example 2 | None | 1139 | 2.58 | 10.03 | 1.57 |
| Comparative Example 3 | None | 1847 | 2.43 | 8.43 | 1.67 |
| Comparative Example 4 | None | 2245 | 2.13 | 7.96 | 1.80 |
| Comparative Example 5 | 1300° C. | 1035 | 15.34 | 2.53 | 1.61 |

(Discussion)

Using the activated carbon obtained in each of Examples 1 to 7 and Comparative Examples 1 to 5, a palladium-carrying activated carbon was produced according to the following palladium-carrying method. The carried amount of palladium of the produced palladium-carrying activated carbon, the degree of dispersion of palladium, and the hydrogenation performance of nitrobenzene were measured according to the following method. Table 2 shows the obtained results.

[Production of Palladium-Carrying Activated Carbon]

The activated carbon of each of Examples and Comparative Examples was pulverized into a powdered activated carbon. 1 g of the powdered activated carbon was added to 20 ml of ion exchange water to prepare a slurry. Meanwhile, 0.0168 g of palladium chloride was dissolved in 20 ml of 0.1 N hydrochloric acid, and a 1N sodium hydroxide solution was then added thereto, to adjust the pH of the palladium chloride solution to about 3.8 to 4.2. While the activated carbon slurry solution was stirred, the palladium chloride solution after the pH adjustment was added to the activated carbon slurry solution, followed by stirring for 15 minutes. Thereafter, a 10% saturated solution of sodium hydrogen carbonate was added to adjust the pH of the solution to 7. Then, the solution was further stirred for 1 hour. Thereafter, 0.8 g of a 37% formaldehyde solution was added to the solution, and the mixture was refluxed at 100° C. for 5 hours in an oil bath to reduce palladium. After the reduction, a catalyst was filtered with a suction filter, and sufficiently washed with ion exchange water. The catalyst was washed, and subjected to vacuum drying at 120° C. to obtain a palladium-carrying activated carbon.

[Measurement of Carried Amount of Palladium of Palladium-Carrying Activated Carbon]

The palladium-carrying activated carbon of each of Examples and Comparative Examples obtained above was subjected to vacuum drying at 120° C. for 2 hours. Then, 0.1 g of the palladium-carrying activated carbon was placed in a decomposition vessel, and 10 ml of 60% nitric acid was then added thereto, followed by mixing. Then, the sample was dissolved using a microwave sample pretreatment device (Discover SP-D80, manufactured by CEM). The dissolved solution was taken out, and adjusted to 25 ml to prepare a measurement solution. The solution was then analyzed using an ICP emission spectrometer (ICPE-9800, manufactured by Shimadzu Corporation). The carried amount of palladium was determined from the obtained value and a calibration curve produced from a palladium standard solution having a known concentration.

[Measurement of Degree of Dispersion of Palladium of Palladium-Carrying Activated Carbon]

The degree of dispersion of palladium was measured by a CO pulse method using Bel-CATII manufactured by MicrotracBEL Corp. The palladium-carrying activated carbon of each of Examples and Comparative Examples was filled in a quartz measuring container. The quartz measuring container was set in the device. A pretreatment was performed in the following procedure. Helium gas was caused to flow at 50 mL/min, and the temperature was raised to 100° C. at a rate of 5° C./min and maintained for 15 minutes. Thereafter, hydrogen gas was caused to flow at 50 mL/min for 20 minutes to perform a reduction treatment. After the reduction treatment, helium gas was caused to flow again at 50 mL/min, and the inside of the measuring container was cooled until the temperature in measuring container was 50° C. After the pretreatment, CO pulse measurement was performed. The adsorbed amount of CO was measured at a measurement temperature of 50° C. using 10% CO/He as an adsorption gas. From the obtained adsorbed amount of CO and the carried amount of palladium calculated by ICP measurement, the degree of dispersion of palladium of the palladium-carrying activated carbon was measured.

[Measurement of Hydrogenation Performance of Nitrobenzene]

Hydrogenation performance was evaluated using a medium-pressure reduction device "CH-200" manufactured by ISHII LABORATORY WORKS CO., LTD. 4.2 ml of nitrobenzene and 25 ml of 2-propanol were added into a reaction vessel, followed by mixing. Then, 50 mg of the palladium-carrying activated carbon of each of Examples and Comparative Examples obtained above was added to the mixture, and dispersed in the solution. The reaction vessel was set in the device. The inside of the vessel was sufficiently replaced with hydrogen gas, and the temperature was then raised to 40° C. The solution was stirred for 15 minutes for stabilization, and hydrogen gas having an initial pressure of 0.35 MPa was then introduced into the reaction vessel to measure the change with time of a hydrogen pressure in the reaction vessel, thereby evaluating hydrogenation performance. The amount of change in the hydrogen pressure from the initial hydrogen pressure after 20 minutes from the reaction was read, and values obtained by dividing the amount of change by the specific surface area of the activated carbon were compared with each other. In the present Example, the value of 1.7E-05 or more is regarded as acceptable.

TABLE 2

| | D50 μm | Supported amount of Pd % by mass | Degree of dispersion of Pd % | Change in hydrogen pressure after 20 minutes from start of reaction MPa | Change in hydrogen pressure after 20 minutes from start of reaction/specific surface area MPa/m$^2$/g |
|---|---|---|---|---|---|
| Example 1 | 5.7 | 0.85 | 17 | 0.026 | 2.38E−05 |
| Example 2 | 5.3 | 0.83 | 27 | 0.033 | 2.39E−05 |
| Example 3 | 6.5 | 0.85 | 26 | 0.036 | 2.22E−05 |
| Example 4 | 6.3 | 0.85 | 17 | 0.039 | 2.05E−05 |
| Example 5 | 5.6 | 0.84 | 22 | 0.027 | 1.96E−05 |
| Example 6 | 6.3 | 0.86 | 29 | 0.024 | 1.78E−05 |
| Example 7 | 7.9 | 0.87 | 16 | 0.026 | 2.07E−05 |
| Comparative Example 1 | 5.3 | 0.86 | 19 | 0.018 | 1.67E−05 |
| Comparative Example 2 | 5.8 | 0.80 | 27 | 0.023 | 1.65E−05 |
| Comparative Example 3 | 6.8 | 0.82 | 29 | 0.029 | 1.57E−05 |
| Comparative Example 4 | 6.7 | 0.82 | 23 | 0.032 | 1.43E−05 |
| Comparative Example 5 | 5.8 | 0.85 | 1 | 0.010 | 9.66E−06 |

(Discussion)

As is clear from the results in Table 2, when the activated carbon obtained in each of Comparative Examples 1 to 5 is used as a palladium carrier, the amount of change in the hydrogen pressure after 20 minutes from the start of the reaction with respect to the specific surface area is small.

Meanwhile, it is clear that, when the activated carbon obtained in each of Examples 1 to 7 is used as a palladium carrier, the amount of change in the hydrogen pressure after 20 minutes from the start of the reaction with respect to the specific surface area is improved regardless of the similar degree of dispersion of palladium, and the hydrogenation performance in the same specific surface area is improved.

This application is based on Japanese Patent Application No. 2017-247439 filed on Dec. 25, 2017, the contents of which are included in the present application.

The present invention has been appropriately and sufficiently explained above by way of the embodiments while referring to the specific examples described above, for the purpose of illustrating the invention. A person skilled in the art should recognize, however, that the embodiments described above can be easily modified and/or improved. Therefore, it is understood that any modified embodiments or improved embodiments conducted by a person skilled in the art are encompassed within the scope as claimed in the appended claims, so long as these modifications and improvements do not depart from the scope of the claims.

INDUSTRIAL APPLICABILITY

The present invention has wide industrial applicability in a technical field related to an activated carbon and a catalyst-carrying activated carbon using the same, and the like.

The invention claimed is:

1. An activated carbon having an electric conductivity of 3.5 to 15 S/cm obtained by powder resistance measurement under a load of 12 kN and an oxygen content of 3.0% by mass or more.

2. The activated carbon according to claim 1, wherein the activated carbon is derived from coconut shell.

3. A metal-carrying activated carbon, wherein a metal is carried on the activated carbon according to claim 1.

4. The metal-carrying activated carbon according to claim 3, wherein the metal is palladium.

5. A hydrogenation method comprising contacting a reaction substrate with a hydrogen source and the metal-carrying activated carbon according to claim 3.

6. A hydrogenation method comprising contacting a reaction substrate with a hydrogen source and the metal-carrying activated carbon according to claim 4.

7. The activated carbon according to claim 1, having an oxygen content of 20.0% by mass or less.

8. The activated carbon according to claim 1, having a BET surface area of 1,000 m$^2$/g or more.

9. The activated carbon according to claim 1, having a BET surface area of 2,200 m$^2$/g or less.

10. The activated carbon according to claim 1, wherein said electric conductivity is 3.5 to 13 S/cm.

11. The activated carbon according to claim 1, wherein said electric conductivity is 3.5 to 10 S/cm.

12. The activated carbon according to claim 1, having an oxygen content of 15.0% by mass or less.

13. The activated carbon according to claim 1, having an oxygen content of 10.0% by mass or less.

14. The activated carbon according to claim 1, having a BET surface area of 1,300 m$^2$/g or more.

15. The activated carbon according to claim 1, having a BET surface area of 1,600 m$^2$/g or more.

16. The activated carbon according to claim 1, having a BET surface area of 2,100 m$^2$/g or less.

17. The activated carbon according to claim 1, having a BET surface area of 2,000 m$^2$/g or less.

18. The activated carbon according to claim 1, having an average pore size of 1.55 nm or more.

19. The activated carbon according to claim 1, having an average pore size of 1.65 nm or more.

20. The activated carbon according to claim 1, wherein an average particle D50 of about 150 μm to 5 mm.

* * * * *